(12) United States Patent
Vaske et al.

(10) Patent No.: US 8,364,028 B1
(45) Date of Patent: Jan. 29, 2013

(54) PLASTIC SCENT POD AND METHOD FOR HEATING A SCENT POD

(75) Inventors: Jason Vaske, Chandler, AZ (US); Brad Pesu, Gilbert, AZ (US); Maxine Pesu, Gilbert, AZ (US); Lynae Parrott, Gilbert, AZ (US)

(73) Assignee: Gold Canyon International, LLC, Chandler, AZ (US)

( * ) Notice: Subject to any disclaimer, the term of this patent is extended or adjusted under 35 U.S.C. 154(b) by 917 days.

(21) Appl. No.: 12/107,962

(22) Filed: Apr. 23, 2008

(51) Int. Cl.
| | |
|---|---|
| *A61L 9/03* | (2006.01) |
| *A61L 9/015* | (2006.01) |
| *F24F 3/12* | (2006.01) |
| *F27B 14/16* | (2006.01) |
| *H05B 3/06* | (2006.01) |
| *B01B 1/00* | (2006.01) |
| *A47G 23/00* | (2006.01) |

(52) U.S. Cl. ........ 392/390; 392/403; 392/405; 219/438; 219/385; 219/386; 220/23.4; 422/5; 422/120

(58) Field of Classification Search .................. None
See application file for complete search history.

(56) References Cited

U.S. PATENT DOCUMENTS

| | | | | |
|---|---|---|---|---|
| 4,781,895 | A * | 11/1988 | Spector | 422/125 |
| 5,647,052 | A * | 7/1997 | Patel et al. | 392/390 |
| 5,651,942 | A | 7/1997 | Christensen | |
| 6,106,786 | A | 8/2000 | Akahoshi | |
| 6,234,786 | B1 | 5/2001 | Wagner | |
| 6,328,935 | B1 * | 12/2001 | Buccellato | 422/125 |
| 6,354,710 | B1 * | 3/2002 | Nacouzi | 362/96 |
| 6,361,752 | B1 | 3/2002 | Demarest et al. | |
| 6,399,027 | B1 * | 6/2002 | Shah et al. | 422/124 |
| 6,413,476 | B1 * | 7/2002 | Barnhart | 422/124 |
| 6,627,857 | B1 * | 9/2003 | Tanner et al. | 219/445.1 |
| 6,733,548 | B2 | 5/2004 | Rasmussen et al. | |
| 7,028,917 | B2 | 4/2006 | Buthier | |
| D522,671 | S | 6/2006 | Niemeyer | |
| 7,067,772 | B2 | 6/2006 | Tanner et al. | |
| 7,132,084 | B1 * | 11/2006 | Roumpos | 422/125 |
| 7,133,605 | B2 | 11/2006 | Niemeyer | |
| 7,195,739 | B1 | 3/2007 | Penman et al. | |
| D542,437 | S | 5/2007 | Snow | |
| 7,329,839 | B2 | 2/2008 | Palmer | |
| 7,548,684 | B2 * | 6/2009 | Berrido et al. | 392/390 |
| 2002/0152672 | A1 | 10/2002 | Rasmussen et al. | |
| 2003/0007887 | A1 * | 1/2003 | Roumpos et al. | 422/1 |
| 2003/0086815 | A1 * | 5/2003 | Wesley | 422/5 |

(Continued)

OTHER PUBLICATIONS

"Samsung Total PP HJ730" High Crystallinity Polypropylene, Datasheet, Mar. 2005. http://prospector.ides.com/DataView.aspx?I=34&TAB=DV_DS&E=82681&SKEY=34.1364975.54118977%3A299551d3-6150-4434-97e9-4341f7a6317b&CULTURE=en-US.*

*Primary Examiner* — Joseph M Pelham
(74) *Attorney, Agent, or Firm* — Booth Udall, PLC

(57) ABSTRACT

A scent pod for scenting the air and methods of use. A scent pod comprises a container having a base and at least one sidewall, wherein a majority of the base and the at least one sidewall is formed of plastic having a thickness of at least 0.1 millimeters. A scented wax inside the container comprises a fragrance and a first temperature at which the scented wax liquefies and evaporates fragrance. The scent pod warmer generates heat at a second temperature hot enough to completely liquefy the scented wax in less than three hours, and the plastic for the container comprising a plastic having a heat deflection temperature high enough to withstand the heat generated by the scent pod warmer without deforming.

19 Claims, 5 Drawing Sheets

U.S. PATENT DOCUMENTS

| | | |
|---|---|---|
| 2004/0033067 A1* | 2/2004 | He et al. .................. 392/395 |
| 2004/0250464 A1 | 12/2004 | Rasmussen et al. |
| 2005/0016985 A1* | 1/2005 | Haas et al. ............... 219/438 |
| 2005/0150886 A1 | 7/2005 | Niemeyer |
| 2005/0163649 A1 | 7/2005 | Friedrich et al. |
| 2006/0006582 A1 | 1/2006 | Strelnieks |
| 2006/0018786 A1 | 1/2006 | Tolman et al. |
| 2006/0163240 A1* | 7/2006 | Xiao ........................ 219/438 |
| 2006/0163241 A1* | 7/2006 | Xiao ........................ 219/438 |
| 2006/0239870 A1 | 10/2006 | Schutte et al. |
| 2006/0240371 A1 | 10/2006 | Palmer |
| 2007/0047931 A1 | 3/2007 | Niemeyer |

* cited by examiner

PLASTIC SCENT POD AND METHOD FOR HEATING A SCENT POD

BACKGROUND

1. Technical Field

Aspects of this document relate generally to heated scent-emitting products.

2. Background Art

Conventional scent-emitting devices exist. Such devices have been used to add fragrance to rooms. Fragrance may be added to a room for purely aesthetic reasons, for purposes of aroma therapy, or to mask undesirable odors such as cooking odors, smoke, mildew and the like. Conventional scent-emitting devices may comprise a fragrance carried in a substrate such as wood, paper, cloth, gel, plastic, ceramic, liquid, or other compound or material suitable for fragrance carrying. Conventional scent-emitting devices rely on air movement, heat, or other energy input in order to effectively disperse a fragrance. Conventional "fragrances" may comprise a simple perfume, an essential oil, or other aroma compound.

Some examples of conventional scent-emitting products more closely related to the present disclosure include scented candles, scented wickless candles (on a warming plate), scented wax chips, and the like. Scented candles and scented wickless candles conventionally are held in glass, ceramic or metal holders (to withstand the flame or heat applied to or by the product or, in the case of some candles, are left free-standing without a container. One particular implementation of a scented wickless candle known in the prior art includes a warmer and scented wax contained in a metal container that includes a metal base and metal sides, with a hard plastic rim glued to the top of the metal sides with a hard plastic lid removably coupled to the hard plastic rim.

SUMMARY

Aspects of this document relate to heated scent-emitting products.

In one aspect, a scent pod for use with a scent pod warmer device comprises a container having a base and at least one sidewall, wherein a majority of the base and the at least one sidewall is formed of plastic having a thickness of at least 0.1 millimeters. Scented wax inside the container is provided, the scented wax comprising a fragrance and a first temperature at which the scented wax liquefies and evaporates fragrance. The scent pod warmer generates heat at a second temperature hot enough to completely liquefy the scented wax in less than three hours. The plastic for the container comprises a plastic having a heat deflection temperature high enough to withstand the heat generated by the scent pod warmer without deforming.

Particular implementations may include one or more of the following. The scent pod may be at least one of translucent and transparent plastic. The base of the container may comprise a flat base surface. The flat base surface may comprise a thickness of at least about 1.0 millimeters. Using this thickness, the heat deflection temperature of unannealed plastic measured using the ASTM standard D648 at a pressure of 66 psi may be at least 257° Fahrenheit without deformation. The scent pod container may possess a Underwriters' Laboratories Relative Temperature Index Strength measured using UL 746 of about 115° Centigrade. A lid removably coupled to the base may be provided. A lip ring coupled to a top edge of the container between the base and the lid may be provided. The removable lid and lip ring may both be formed of plastic, and may both be formed of the same plastic the majority of the container is formed of. The heat deflection temperature of the plastic may be such that the heat from the scent pod warmer completely liquefies the scented wax in less than two hours without deforming the container. The heat deflection temperature of the plastic may be such that the heat from the scent pod warmer completely liquefies the scented wax in less than one hour without deforming the container.

In another aspect, a system for scenting the air in a room with scent from a scent pod comprises a scent pod warmer configured to generate heat at a first temperature. A container having a majority of the container formed of plastic, the container comprising a scent emitter therein, the scent emitter having a fragrance and a second temperature at which the fragrance evaporates is provided. The first temperature is large enough to evaporate at least a portion of the fragrance from the scent emitter in the plastic container in less than three hours without deforming the plastic of the container.

Particular implementations may include one or more of the following. The first temperature may be set so that it is no greater than 230° Fahrenheit. The container may comprise a flat bottom surface. The flat bottom surface may comprise a thickness of at least about 1.0 millimeters. Using this thickness, unannealed plastic may comprise a heat deflection temperature measured using the ASTM standard D648 at a pressure of 66 psi of at least 257° Fahrenheit without deformation.

In still another aspect, a method for scenting the air in a room from a scent pod, the method comprises placing a plastic base of a scent pod container on a scent pod warmer surface, the scent pod container comprising a scented wax and fragrance within the container. The method also comprises heating the plastic base of the scent pod container through the scent pod warmer surface by heating the scent pod warmer surface to a temperature sufficient to completely liquefy the wax and evaporate at least a portion of the fragrance in less than 3 hours without deforming the plastic base.

Particular implementations may include one or more of the following. The plastic base of the scent pod container may be heated to a temperature sufficient to completely liquefy the wax and evaporate at least a portion of the fragrance in less than 2 hours. The plastic base of the scent pod container may be heated to a temperature sufficient to completely liquefy the wax and evaporate at least a portion of the fragrance in less than 1 hour.

In yet another aspect, a method for scenting the air in a room from a scent pod comprises placing a plastic base of a scent pod container on a scent pod warmer surface, the scent pod container having a scent emitter comprising a fragrance within the container. Heating the plastic base of the scent pod container through the scent pod warmer surface by heating the scent pod warmer surface to a temperature sufficient to evaporate at least a portion of the fragrance from the scent emitter in less than 3 hours without deforming the plastic base is provided.

Particular implementations may include one or more of the following. The plastic base of the scent pod container may be heated to a temperature sufficient to completely liquefy the wax and evaporate at least a portion of the fragrance from the scent emitter in less than 2 hours. The plastic base of the scent pod container may be heated to a temperature sufficient to completely liquefy the wax and evaporate at least a portion of the fragrance from the scent emitter in less than 1 hour.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DESCRIPTION

Figure 1:
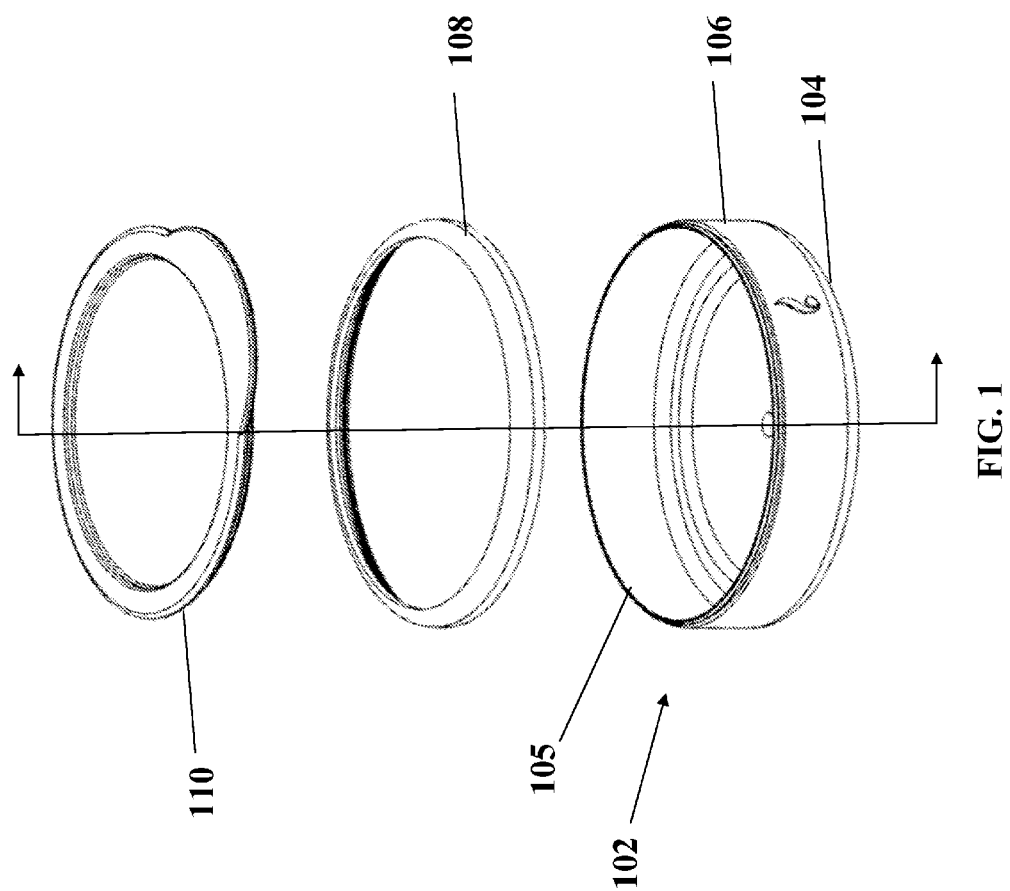
FIG. 1 is a break apart view of a scent pod container.

This disclosure, its aspects and implementations are not limited to the specific components or assembly procedures disclosed herein. Many additional components and assembly procedures known in the art consistent with the intended operation and/or assembly procedures for a scent pod and heating system and method will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such scent pods and implementing components, consistent with the intended operation. In addition, there are many features of a scent pod disclosed herein, of which one, a plurality, or all features may be used in any particular implementation.

It will be understood that scent pod and heating system implementations are not limited to the specific assemblies, devices and components disclosed in this document, as virtually any assemblies, devices and components consistent with the intended operation of a scent pod implementation may be utilized. Accordingly, for example, although particular scent pods, bases, side walls, brims, lip rings, removable lids, heating elements, and other assemblies, devices and components are disclosed, such may comprise any shape, size, style, type, model, version, class, measurement, concentration, material, weight, quantity, and/or the like consistent with the intended operation of a scent pod implementation. Implementations are not limited to uses of any specific assemblies, devices and components; provided that the assemblies, devices and components selected are consistent with the intended operation of a scent pod and heating system implementation.

Implementations of scent pods and implementing components may be constructed of a wide variety of materials. For example, the components may be formed of: polymers such as thermoplastics (such as Polypropylene, ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; glasses (such as fiberglass), carbon-fiber, aramid-fiber, any combination thereof, and/or other like materials; composites and/or other like materials; metals, such as zinc, magnesium, titanium, copper, lead, iron, steel, carbon steel, alloy steel, tool steel, stainless steel, brass, tin, antimony, aluminum, any combination thereof, and/or other like materials; alloys, such as aluminum alloy, titanium alloy, magnesium alloy, copper alloy, any combination thereof, and/or other like materials; any other suitable material; and/or any combination of the foregoing thereof. For the exemplary purposes of this disclosure, components of a scent pod container may comprise a plastic material like polypropylene.

Some components defining a scent pod and scent pod assembly implementations may be manufactured simultaneously and integrally joined with one another, while other components may be purchased pre-manufactured or manufactured separately and then assembled with the integral components. Various implementations may be manufactured using conventional procedures as added to and improved upon through the procedures described here.

Accordingly, manufacture of these components separately or simultaneously may involve injection molding, vacuum forming, blow molding, casting, forging, cold rolling, milling, drilling, reaming, turning, grinding, stamping, pressing, cutting, bending, welding, soldering, hardening, riveting, punching, plating, and/or the like. Components manufactured separately may then be coupled or removably coupled with the other integral components in any manner, such as with adhesive, a heat weld, a weld joint, a solder joint, a fastener (e.g. a bolt and a nut, a screw, a rivet, a pin, and/or the like), washers, retainers, wrapping, wiring, any combination thereof, and/or the like for example, depending on, among other considerations, the particular material forming the components.

It has been determined that for most social gatherings where a scent pod and scent pod warmer surface is used, it is most desirable if fragrance begins to evaporate within 3 hours, and more desirable that it evaporate within 2 hours. In particular implementations, it is desirable for fragrance to evaporate in less than 1 hour. For specific implementations where the scent emitter is scented wax, it is desirable if the fragrance evaporates from the liquefied wax within 3 hours, or more preferably in less than 2 hours. In particular implementations, it is desirable for the scented wax to completely liquefy and fragrance to evaporate in less than 1 hour.

It is believed that, different from the conventional ceramic, glass and metal containers, a plastic container will be more desirable from a safety and marketing standpoint and that it will provide production advantages as well. However the use of plastic as a container on a heating element, and particularly on a heating element when the plastic container contains melted wax presents its own safety and use concerns. One challenge in using a plastic container is that plastic itself can melt from the heating element, causing the sides of the plastic container to deform and present safety hazards. The use of wax inside the plastic container compounds the heating problems. To use a plastic container, a balance needs to be had between the temperature of the scent pod warmer surface, the melting point of the scented wax (if used), the thickness of the wax (if used), and the plastic used to form the plastic container. If the temperature is too high or the plastic heat deflection temperature of the plastic too low, the plastic may melt when exposed too long to the warmer surface. Additionally, if the wax has too high a melting point or is too thick, the wax may not liquefy completely from the heat of the warmer plate resulting in an ineffective fragrance dispursement.

Figure 2:
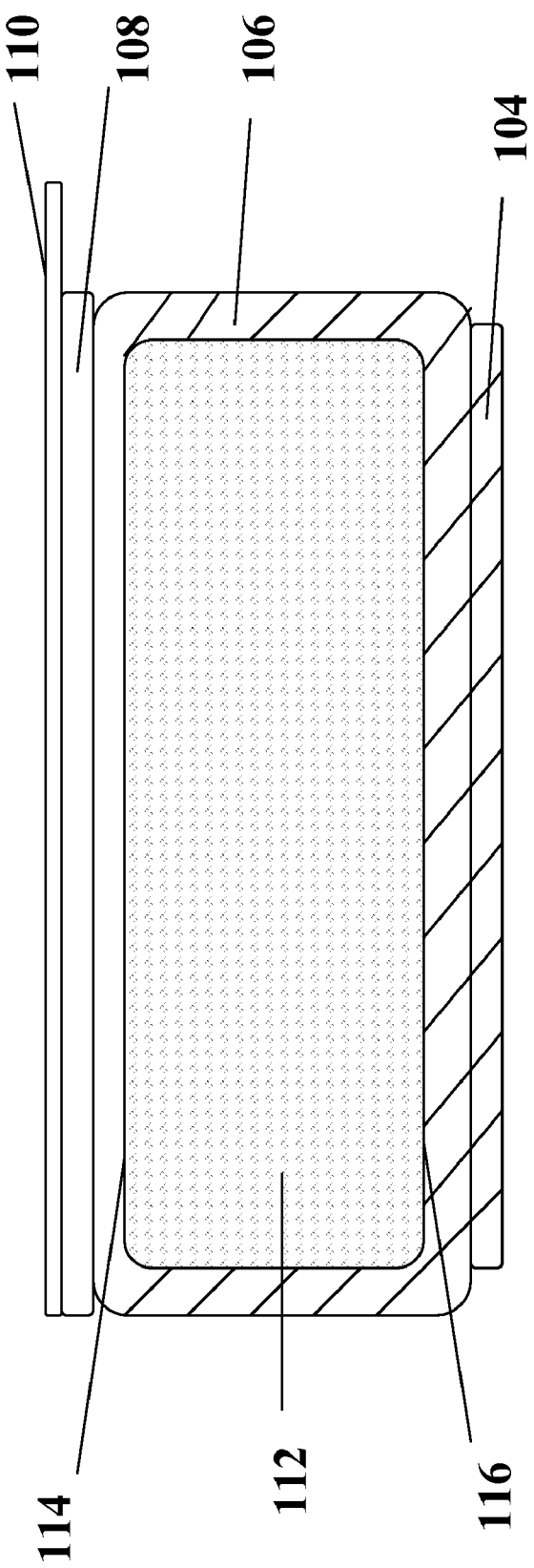
FIG. 2 is a cross sectional view of a scent pod container.

With reference to FIGS. 1-2, a break apart view and a cross-sectional view of a scent pod container are illustrated, respectively. Scent pod 100 may comprise base 104, brim 105, and side wall 106, lip ring 108, and removable lid 110. Scent pod container 102 may comprise base 104, brim 105, and side wall 106. The components defining scent pod 100 may be formed integrally or formed separately and then joined together. For this particular implementation, scent pod container 100 (and one or more components thereof) may be formed with a majority of the container 100 made of plastic having a thickness of at least 0.1 millimeters (mm). In other particular implementations, portions of the scent pod container 100 may be formed to include some other materials, such as, by non-limiting example, a metal base or metal portions of the sides. In some implementations, lip ring 108 may be removably coupled with brim 105. Removable lid 106 may be removably coupled with scent pod container 102 via lip ring 108, or directly with the brim 105 of the base 104 in implementations where no lip ring 108 is used. Base 104 may comprise a flat base surface. In other particular implementations, a curved base surface may be used, but it is desirable to have the shape of the scent pod base surface mate with the surface of the scent pod warmer surface to enable more efficient heat transfer. It is not required, however, that they mate exactly.

In one particular implementation shown in FIG. 1, the material comprising the flat base surface has a thickness of at least 1.0 millimeters (mm) and is formed of a translucent or a transparent plastic. The plastic forming scent pod 100 (and/or its components) may comprise a heat deflection temperature measured using ASTM standard D648 at a pressure of 66 psi of at least 257° Fahrenheit without deformation for unannealed plastic. It will be understood that "heat deflection temperature" refers to the temperature at which a plastic deforms. For safety, scent pods are required to withstand temperatures much higher than a typical warmer surface will generate, and for a much longer time. Accordingly, research was conducted and numerous plastics were tested in determining which plastics could withstand the rigorous testing processes while the scented wax liquefied and yet provide translucent or transparent view of the scented wax within the container. There are very few plastics which are transparent or translucent and which also have a heat deflection temperature of at least 257° Fahrenheit. Samsung Total HJ730 plastic by Samsung Total Petrochemicals Co., Ltd. Is one found to work for the specific examples provided in this disclosure. This plastic also comprises a Underwriters' Laboratories Relative Temperature Index Strength (UL RTI) measured using UL 746 of at least 115° Centigrade. It will be understood that UL RTI refers to a material's thermal endurance. In particular, UL RTI is used to determine the effective life of a plastic article, determined by accelerated aging or deterioration of the plastic at elevated temperatures.

Still referring to FIGS. 1-2, scent pod container 102 may contain a scent emitter 112 in the form of scented wax 112, which comprises a scented wax bottom surface 116 in surface communication with base 104, and scented wax upper surface 114. Scented wax 112 may comprise any animal wax, vegetable wax, mineral wax, petroleum wax or synthetic wax in compound with a fragrance. A fragrance may comprise any perfume, essential oil, or other aromatic compound, whether derived from a plant source, animal source, other natural source, or any synthetic source. It will be understood that where liquid fragrance is compounded with wax, the liquid fragrance may remain in its liquid state and may reside in the interstitial spaces between individual wax crystals. In one particular implementation shown in FIG. 1, the scented wax 112 is formed of the same wax scented candles are made of. One example of a company that manufactures and sells scented candles is Gold Canyon International, Inc. of Arizona, USA. Wax, depending upon its physical properties related to the type of wax used, has a temperature at which it melts. Scented wax is wax that includes fragrance mixed with the wax. When the wax melts from a solid to a liquid, the fragrance trapped in the previously solid wax now turned liquid begins to evaporate. In a particular implementation of scented wax 112, the temperature at which scented wax 112 liquefies and evaporates fragrance is between 140° and 170° Fahrenheit. In other implementations, the temperature at which scented wax 112 liquefies and evaporates fragrance is above about 113° Fahrenheit.

Figure 5:
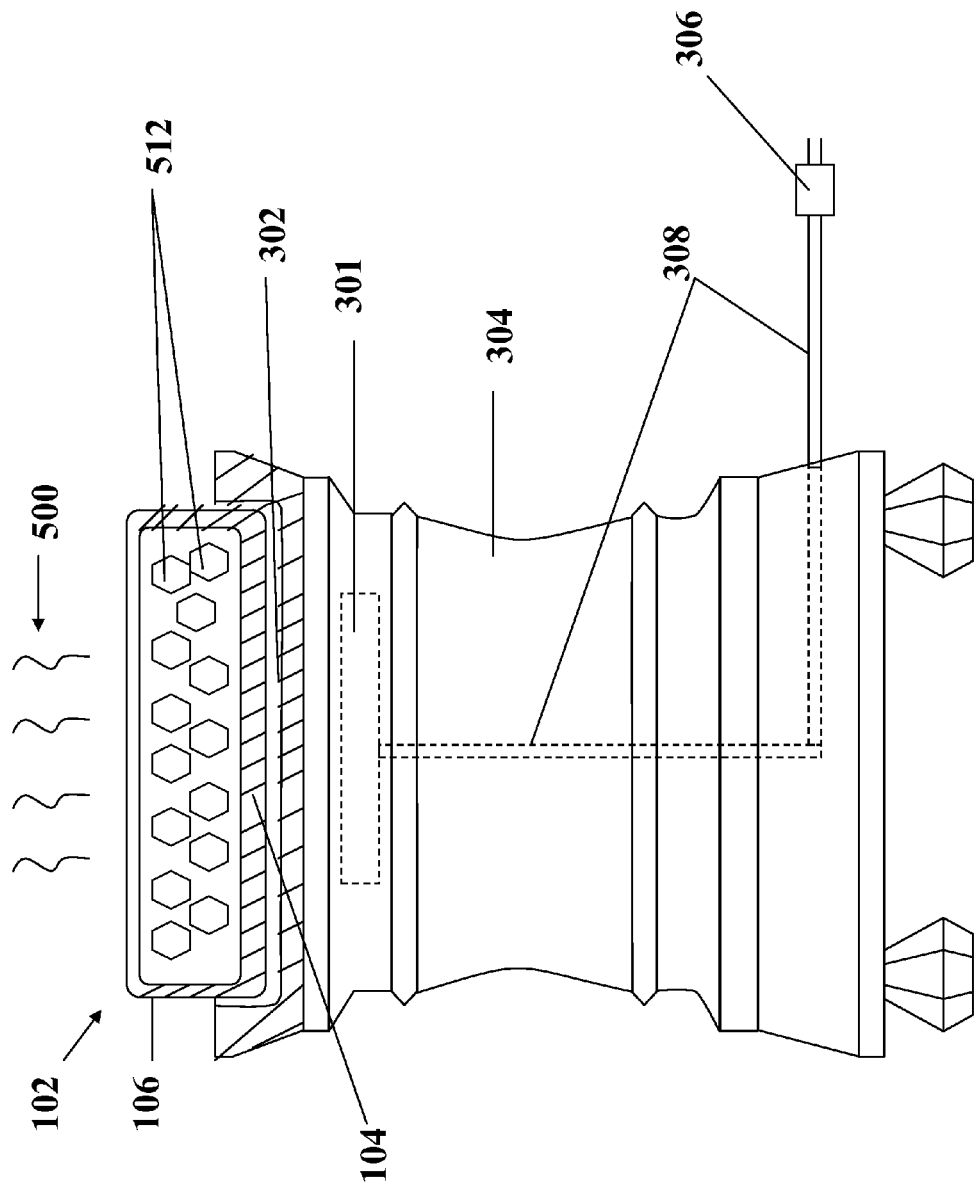
FIG. 5 is an in-use view of a scent pod containing a second form of a scent emitter placed on a scent pod warmer.

In particular implementations, and as shown in the in-use view provided in FIG. 5, scent pod container 102 may contain a scent emitter in other forms. Other forms of scent emitters include any substrate capable of carrying a fragrance such as, without limitation, wood, paper, cloth, felt, gel, plastic, ceramic, glass, liquid, or other compound or material suitable for carrying a fragrance. It will be understood that, in implementations involving a scent emitter, the scent emitter may first be formed and thereafter impregnated with a fragrance, or the substrate may be impregnated with fragrance simultaneously with its forming.

Figure 3:
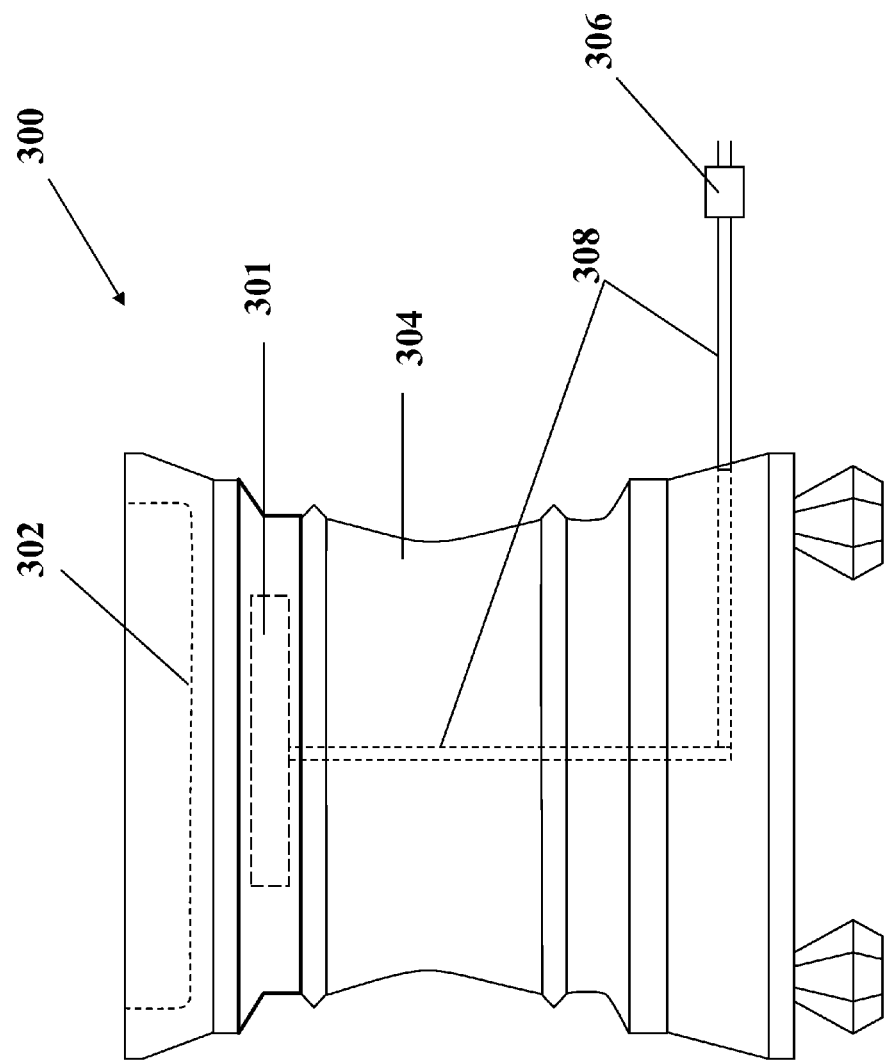
FIG. 3 is a perspective view of a scent pod warmer.

FIG. 3 illustrates a perspective view of a scent pod warmer. Scent pod warmer 300 may comprises scent pod warmer surface 302 and warmer base 304. The scent pod warmer surface 302 is heated with electricity or a flame in limited implementations, or other heating element. In the particular implementation illustrated in FIG. 3, the scent pod warmer surface 302 comprises electric resistor 301, which may be in electrical communication with a power outlet via power plug 306 and electrical cord 308. Other heating elements are known in the art and are equally interchangeable with the non-limiting example provided here. Those of ordinary skill in the art can readily select appropriate materials for creating a warmer surface with a desired temperature. With power plug 306 inserted in a power outlet, electricity flows through electrical cord 308 to electrical resistor 301. Electrical resistor 301 converts the electrical energy into heat energy. In particular implementations, scent pod warmer surface 302 itself may comprise electrical resistor 301 or other resistive or other heating element. In other implementations, electrical resistor 301 may be coupled with scent pod warmer surface 302 or adjacent to or separated from scent pod warmer surface 302. In particular implementations, for safety, the temperature of scent pod warmer surface 302 is designed so that it does not exceed 230° Fahrenheit.

Figure 4:
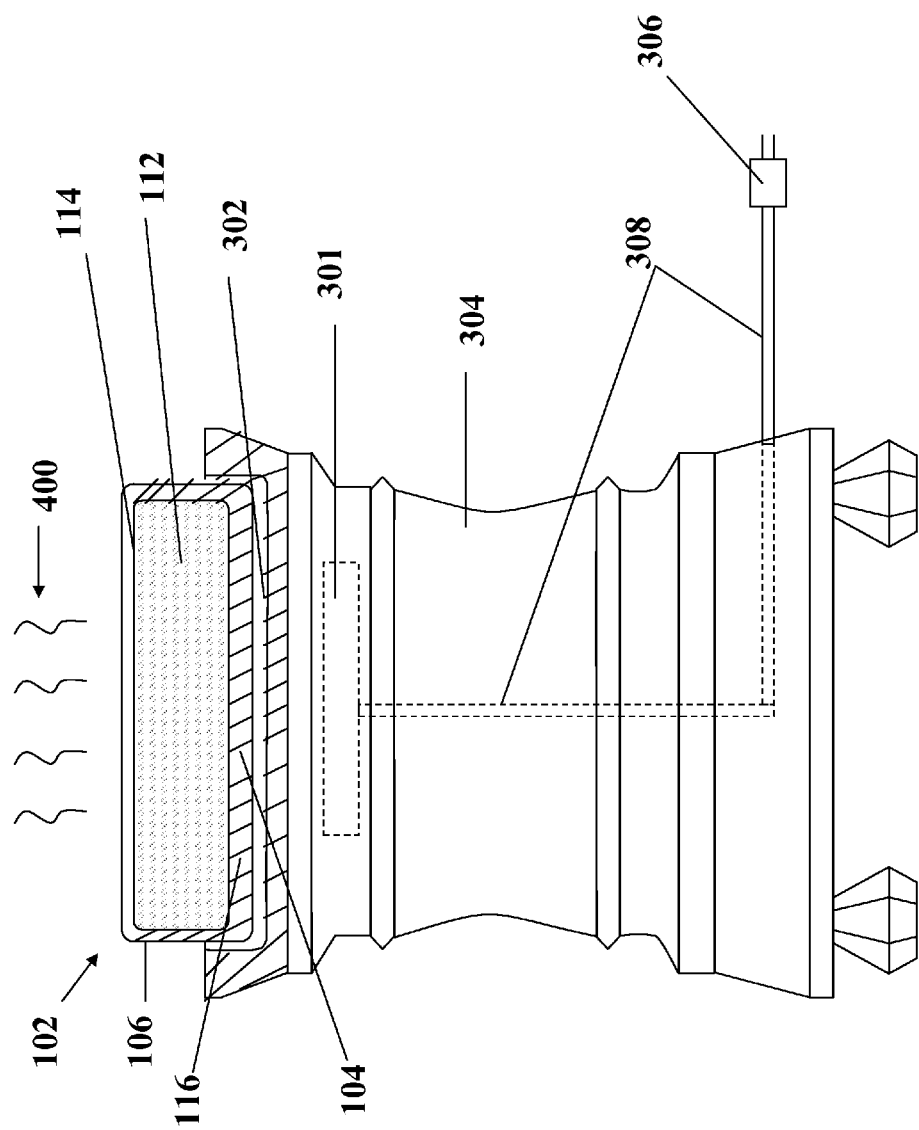
FIG. 4 is an in-use view of a scent pod containing a scent emitter in the form of a scented wax, the scent pod placed on a scent pod warmer.

Referring to FIG. 4, an in-use view of a scent pod containing scented wax and placed on a scent pod warmer is illustrated. A user may place scent pod container 102 on scent pod warmer 300 so that base 104 of scent pod container 102 is in thermal communication with scent pod warmer surface 302 of scent pod warmer 300. When the temperature of scent pod warmer surface 302 begins to increase (with base 104 of scent pod container 102 placed thereupon), the plastic comprising base 104 also begins to increase in temperature. Additionally, the thermal energy conducted from scent pod warmer surface 302 through base 104 continues to be conducted to scented wax bottom surface 116, through scented wax 112, until it escapes through scented wax upper surface 114 (which may carry fragrance 400 with it). When heated from the bottom through the plastic comprising the base 104, the scented wax 112 liquefies beginning with the scented wax bottom surface 116, slowly through the scented wax 112 until the scented wax upper surface 114 liquefies. Generally, the scented wax upper surface 114 begins liquefying at the center and moves outward to the edges until all of the scented wax upper surface 114, and all of the scented wax 112 below it, is completely liquefied.

The surface area of the liquefied scented wax upper surface 114 determines the amount of fragrance that evaporates from the scented wax 112. The greatest fragrance evaporation efficiency occurs when scented wax upper surface 114 has completely liquefied. For the scented wax 112 used in the particular implementation described above, the scented wax liquefies most efficiently, and safely, at a temperature range of between 140° and 170° Fahrenheit. It was found through testing that with approximately ¾ inches thick of scented wax in a plastic container having a base thickness of around 1.8 millimeters and an opening diameter of about 3¼ inches, the scented wax could be completely liquefied in the plastic container in less than 3 hours without deforming the plastic container and with the plastic container passing its standard safety tests. Temperatures closer to the bottom of the range yielded a longer melting time than temperatures closer to the top of the range. In other implementations, scented wax 112 takes less than two hours to completely liquefy. In still other implementations, scented wax 112 takes less than one hour to completely liquefy. It will be understood that the time in which scented wax 112 completely liquefies may vary depending upon the temperature of scent pod warmer surface 302, the thickness of base 104 of scent pod container 102, the thickness of scented wax 112 within scent pod container 102, the melting point of scented wax 112, the ambient room temperature, and other factors.

Still referring to FIG. 4, scent pod warmer surface 302 may be required to generate sufficient heat to completely liquefy scented wax 112 in less than three hours without deforming the plastic comprising scent pod 100. Accordingly, in particular implementations, the plastic forming scent pod 100 has a sufficient heat deflection temperature to withstand the heat generated by scent pod warmer surface 302 without deforming. Although the heat deflection temperature of the plastic used in the example with reference to FIG. 1 is 257° Fahrenheit, plastics with other heat deflection temperatures are also possible and contemplated. The number of possibilities of different heat deflection temperatures, wax melting points, warmer surface temperatures, plastic thicknesses and ambient temperatures is too great to provide all examples and it is believed that one of ordinary skill in the relevant art can readily design other plastic scent pod containers for use with scent pod warmers that heat to efficiently disperse fragrance from a scent emitter in a desirable time without deforming the plastic.

FIG. 5 illustrates an in-use view of a scent pod containing another example of a scent emitter placed on a scent pod warmer. Just as with the non-limiting example provided in FIG. 4, a user may place scent pod container 100 on scent pod warmer 300 so that base 104 of scent pod container 102 is in thermal communication with scent pod warmer surface 302 of scent pod warmer 300. When the temperature of scent pod warmer surface 302 begins to increase (with base 104 of scent pod container 102 placed thereupon), the plastic comprising base 104 begins to increase in temperature. Additionally, the thermal energy conducted from scent pod warmer surface 302 through base 104 is conducted to scent emitter 512 (which may comprise a substrate and a fragrance 500). In particular implementations, the substrate is a plastic bead infused with fragrance during production. As the plastic bead heats, it softens and a portion of the fragrance is permitted to evaporate from the plastic bead. In other particular implementations, a gel bead may be used.

As the scent emitter 512 increases in temperature, at least a portion of the fragrance 500 evaporates. In some implementations, with scent pod warmer surface 302 at a temperature of about 150° to 170° Fahrenheit, a portion of the fragrance may take less than three hours to evaporate. In other implementations, a portion of the fragrance may take less than two hours to evaporate. In still other implementations, a portion of the fragrance may take less than one hour to evaporate. It will be understood that the time in which a portion of the fragrance evaporates may vary depending upon the temperature of scent pod warmer surface 302, the thickness of base 104 of scent pod container 102, the amount of scent emitter within scent pod container 102, the ambient room temperature, and other factors. Selection of a suitable plastic for the container may be made using the principles discussed with reference to the example of FIG. 4.

Still referring to FIG. 5, scent pod warmer surface 302 is configured to generate sufficient heat to evaporate a portion of fragrance comprising scent emitter 512 in less than three hours without deforming the plastic comprising scent pod 100. Accordingly, in implementations, the plastic forming scent pod 100 may have a sufficient heat deflection temperature to withstand the heat generated by scent pod warmer surface 302 without deforming. Heating a plastic container, and particularly a transparent or translucent plastic container without the hot wax inside applies less stress to the sides of the plastic container because the hot liquid is not pressing out on the sides, but still requires careful selection of a suitable plastic and heating temperature ranges.

In places where the description above refers to particular implementations of a scent pod, it should be readily apparent that a number of modifications may be made without departing from the spirit thereof and that these implementations may be applied to other scent pods. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

The invention claimed is:

1. A scent pod for use with a scent pod warmer device, the scent pod comprising:
   a container having a base and at least one sidewall, wherein a majority of the base and the at least one sidewall is formed of unannealed plastic having a thickness of at least 0.1 millimeters, the base comprising a flat base surface;
   a single, continuous volume of a scented wax inside the container, the scented wax comprising a fragrance and a first temperature at which the scented wax liquefies and evaporates fragrance;
   wherein the scent pod warmer generating surface heat at a second temperature hot enough to completely liquefy the scented wax in less than three hours, the plastic for the container comprising a thermoplastic having a heat deflection temperature, measured using ASTM D648 at a pressure of 66 psi, of at least 257° Fahrenheit to withstand the heat generated by the scent pod warmer without deforming.

2. The scent pod of claim 1, wherein the plastic is at least one of translucent and transparent.

3. The scent pod of claim 1, wherein the flat base surface comprises a thickness of at least 1.0 millimeters.

4. The scent pod of claim 1, wherein the scent pod container possesses a Underwriters' Laboratories Relative Temperature Index Strength measured using UL 746 of at least 115° Centigrade.

5. The scent pod of claim 1, further comprising a lid removably coupled to the base.

6. The scent pod of claim 5, further comprising a lip ring coupled to a top edge of the contain between the base and the lid.

7. The scent pod of claim 6, wherein the removable lid and lip ring are both formed of plastic.

8. The scent pod of claim 1, wherein the heat deflection temperature of the plastic is such that the heat from the scent pod warmer completely liquefies the scented wax in less than two hours without deforming the container.

9. The scent pod of claim 1, wherein the heat deflection temperature of the plastic is such that the heat from the scent pod warmer completely liquefies the scented wax in less than one hour without deforming the container.

10. The scent pod of claim 1, further comprising a lid removably coupled to the base.

11. The scent pod of claim 10, further comprising a lip ring coupled to a top edge of the contain between the base and the lid.

12. The scent pod of claim 11, wherein the removable lid and lip ring are both formed of plastic.

13. A system for scenting the air in a room from a scent pod, the system comprising:
   a scent pod warmer configured to generate heat at a fixed, nonadjustable surface temperature;
   a container having a majority of the container formed of plastic, the container comprising a flat bottom surface comprising a thickness of at least 1.0 millimeters, the container further comprising a scent emitter therein, the scent emitter having a solid fragrance at room temperature and an evaporation temperature at which the fragrance evaporates;
   wherein the surface temperature is large enough to completely liquefy the solid fragrance in the plastic container in less than three hours without deforming the plastic of the container; and
   wherein the plastic is unannealed plastic comprising a heat deflection temperature of at least 257° Fahrenheit when measured using ASTM D648 at a pressure of 66 psi.

14. The pod warming system of claim 13, wherein the surface temperature is no greater than 230° Fahrenheit.

15. A scent pod for use with a scent pod warmer device, the scent pod comprising:
   a container having a base and at least one sidewall, wherein a majority of the base and the at least one sidewall is formed of plastic having a thickness of at least 0.1 millimeters, the base comprising a flat base surface, the container possessing an Underwriters' Laboratories Relative Temperature Index Strength measured using UL 746 of at least 115° Centigrade;
   a single, continuous volume of a scented wax inside the container, the scented wax comprising a fragrance and a first temperature at which the scented wax liquefies and evaporates fragrance;
   wherein the scent pod warmer generating surface heat at a second temperature hot enough to completely liquefy the scented wax in less than three hours, the plastic for the container comprising a thermoplastic having a heat deflection temperature high enough to withstand the heat generated by the scent pod warmer without deforming.

16. The scent pod of claim 15, wherein the plastic is at least one of translucent and transparent.

17. The scent pod of claim 15, wherein the flat base surface comprises a thickness of at least 1.0 millimeters.

18. The scent pod of claim 15, wherein the heat deflection temperature of the plastic is such that the heat from the scent pod warmer completely liquefies the scented wax in less than two hours without deforming the container.

19. The scent pod of claim 15, wherein the heat deflection temperature of the plastic is such that the heat from the scent pod warmer completely liquefies the scented wax in less than one hour without deforming the container.

\* \* \* \* \*